United States Patent
Hofmann et al.

(10) Patent No.: US 7,508,952 B2
(45) Date of Patent: Mar. 24, 2009

(54) ACOUSTIC SOUND ROUTING IN VEHICLES

(75) Inventors: Marcus Hofmann, Stuttgart (DE);
Klaus Linhard, Schelklingen (DE)

(73) Assignee: Daimler AG, Stuttgart (DE)

( * ) Notice: Subject to any disclaimer, the term of this patent is extended or adjusted under 35 U.S.C. 154(b) by 663 days.

(21) Appl. No.: 10/535,147

(22) PCT Filed: Nov. 20, 2003

(86) PCT No.: PCT/EP03/12989

§ 371 (c)(1),
(2), (4) Date: May 16, 2005

(87) PCT Pub. No.: WO2004/049755

PCT Pub. Date: Jun. 10, 2004

(65) Prior Publication Data

US 2006/0056650 A1     Mar. 16, 2006

(30) Foreign Application Priority Data

Nov. 28, 2002 (DE) ................................ 102 55 794

(51) Int. Cl.
*H04R 1/02* (2006.01)

(52) U.S. Cl. ........................ 381/348; 381/388

(58) Field of Classification Search .................... 381/86, 381/348, 386, 387, 388, 389
See application file for complete search history.

(56) References Cited

U.S. PATENT DOCUMENTS

| | | | |
|---|---|---|---|
| 3,944,757 A * | 3/1976 | Tsukamoto | 381/348 |
| 5,170,435 A * | 12/1992 | Rosen et al. | 381/86 |
| 5,248,846 A * | 9/1993 | Koike et al. | 84/718 |
| 7,130,440 B2 * | 10/2006 | Maekawa et al. | 381/86 |

* cited by examiner

*Primary Examiner*—Brian Ensey
(74) *Attorney, Agent, or Firm*—Patent Central LLC; Stephan A. Pendorf

(57) ABSTRACT

To ensure the same high quality of acoustic radiation from audio systems on each seat of current vehicles, an acoustic device is provided for generating audio signals, which allows sound sources to be integrated into the area located near the headrest of a vehicle seat such that the volume can be regulated in an individual manner without unduly disturbing the other passengers in a vehicle. The headrest does not comprise any loudspeakers, thus is safe regarding accident protection. The acoustic near field at the headrest is generated by means of a sound channel. The loudspeaker is disposed inside the backrest or under the seat, for example, while the sound channel terminates in the headrest. Tuned pipes, the end of which is adjusted to the acoustic impedance of the clearance zone, are used as a sound channel.

13 Claims, 5 Drawing Sheets

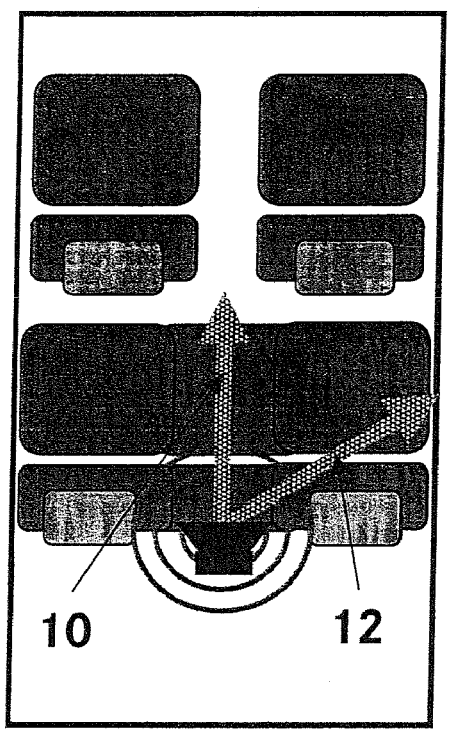 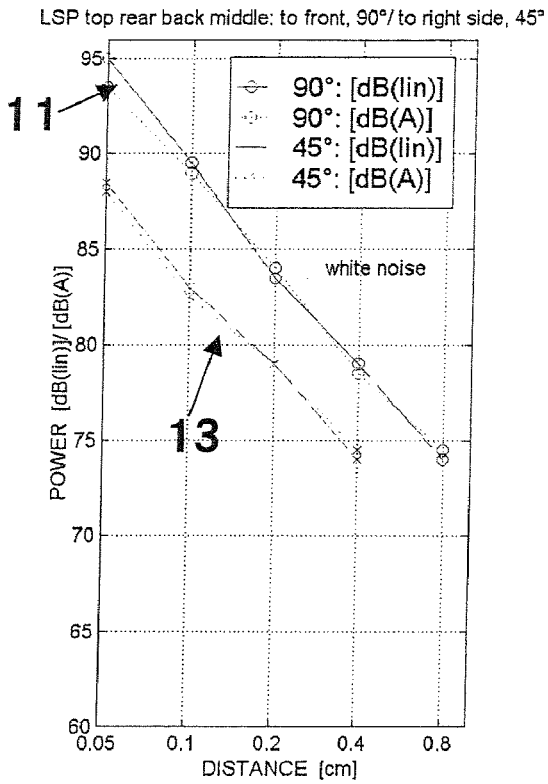
Fig. 1a    Fig. 1b
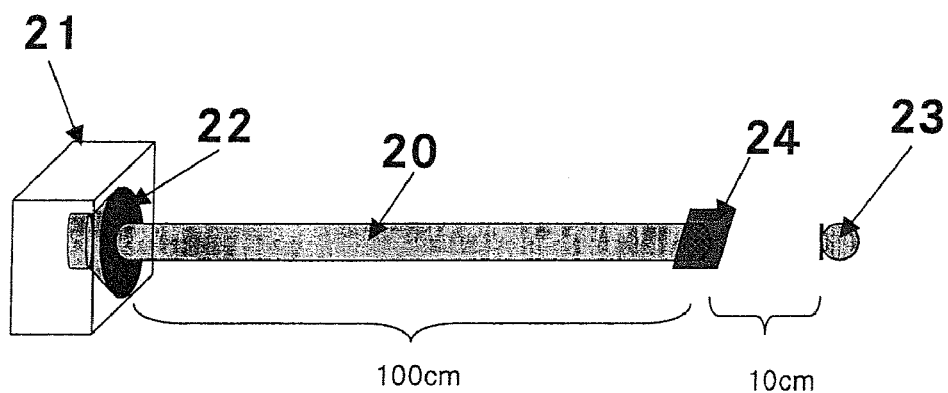
Fig. 2

ACOUSTIC SOUND ROUTING IN VEHICLES

CROSS REFERENCE TO RELATED APPLICATION

This application is a national stage of PCT/EP2003/012989 filed Nov. 20, 2003 and based upon DE 102 55 794.2 filed Nov. 28, 2002 under the International Convention.

BACKGROUND OF THE INVENTION

1. Field of the Invention

The invention relates to an acoustic apparatus for producing audio signals.

2. Related Art of the Invention

Audio diffusion in vehicles today is intended to ensure the same level of quality in every seat. The aim is for all occupants to hear virtually the same audio signal at the same quality and at the same volume; in complex systems, this includes with a stereo or surround effect. Normally, however, commercial appliances today allow only coarse balancing of the volume between "right" and "left" and between "front" and "back". Finer volume adjustment for each seat is not possible. Techniques are known which are aimed at separating the audio output so that people who are physically next to one another can be provided with quite different audio programs. Thus, by way of example, WO 01/08449 A1 describes a method for reproducing audio sound using ultrasound loudspeakers, where the audio signal to be reproduced is linked by amplitude modulation to a carrier signal in the ultrasound frequency range. Such techniques are used to focus the sound using a modulated ultrasound signal. In this context, the audible audio sound is produced along the ultrasound beam radiated at a very high level on account of the nonlinearity of the air and is added up in sharply focused form.

An option for producing audio directly in the headrest of a vehicle seat is demonstrated in patent application EP 1 077 156 A1, for example. In this case, the loudspeaker is integrated in the headrest. The sound emerges through an integrated resonator in the form of a horn, which adjoins the loudspeaker. Another option for producing audio in the headrest with directivity is described in the specification EP 1 077 583 A2. In this case, the directivity is produced by also making use of the sound transmitted toward the back of the headrest from the loudspeaker integrated in the headrest. The general benefit of audio diffusion as a near field in the head region is that the person in direct proximity is provided with good diffusion of sound and people a little further away are provided with a significantly reduced volume of diffused sound. In addition, the diffusion of sound at the headrest provides a good way of achieving spatial audio effects such as stereo. A drawback of these arrangements in which the acoustic system's loudspeaker is directly in the headrest is the reduced accident safety, in particular, since relatively large hard objects are integrated in the otherwise soft headrest and could result in head injuries. In addition, integrating relatively large-volume loudspeakers greatly restricts the visual design options for the headrest.

The specification JP 04 172 795 A describes an acoustic apparatus in which the sound transducer and the sound emergence location are physically separate from one another. In this context, the sound is routed between the sound transducer and the sound emergence location by a tubular sound line. For acoustic impedance matching of the air within the sound line to the environment, a horn-like line termination is proposed. In this case, the line termination is preferably created by means of suitable shaping of sound-absorbing material in order to damp reflections. The patent DE 689 19 495 T2 describes a similar system with sound transmission between the sound transducer and the sound emergence location, the acoustic impedance matching in this case being effected by placing ring elements at the sound emergence opening. In this case, the material from which these ring elements are made has a permeability which corresponds to that of air. In this context, the additional application of the ring elements increases the dimensions of the emergence openings of the sound line, however.

SUMMARY OF THE INVENTION

It is an object of the invention to provide an acoustic apparatus which firstly has no large-volume hard components in the proximity of its sound emergence location and secondly has the best possible matching for the acoustic impedance between the air column produced by a sound transducer and the ambient air.

The object is achieved by virtue of the inventive refinement of an acoustic apparatus for producing audio signals, in which the sound transducer and at least one sound emergence location are physically separate from one another. Such apparatuses have an air-guiding sound line which is connected to the sound emergence location and where a means is provided for achieving acoustic impedance matching for the air in the sound line and the ambient air in order to reduce resonance effects. In this case, the means for acoustic resonance matching is made of a material which has the acoustic impedance of air. In inventive fashion, this material is now placed in two dimensions and conclusively over the at least one sound emergence opening. This advantageously achieves acoustic impedance matching which not only requires the smallest possible physical space but also provides protection from the entry of dirt into the apparatus at the same time.

In particularly advantageous fashion, the material which has the acoustic impedance of air is made of a fibrous and/or porous material, particularly felt, sponge material, unwoven fabric or felt metal. Since the acoustic impedance of air is 41.4 rayl, the material used to terminate the sound line should likewise have a rayl value in this order of magnitude. Commercially, materials called felt metal, for example, which have corresponding rayl values can be obtained without difficulty. The sealing of the end of the tube with material which has a value of approximately 40 rayl simulates a tube of infinite length and thus results in ideal resonance-free emergence of sound. In particularly advantageous fashion, the thickness of the felt metal used should be in the order of magnitude of 1 mm, so that there is firstly adequate shock and compression resistance and secondly the lowest possible damping of the sound waves which are to be transmitted.

BRIEF DESCRIPTION OF THE DRAWINGS

The invention will be described in detail below with reference to exemplary embodiments and figures.

FIG. 1 shows the influences existing within a motor vehicle on the dissemination of acoustic sound waves.

FIG. 2 shows a laboratory design for an acoustic apparatus based on the invention.

DETAILED DESCRIPTION OF THE INVENTION

Figure 3:
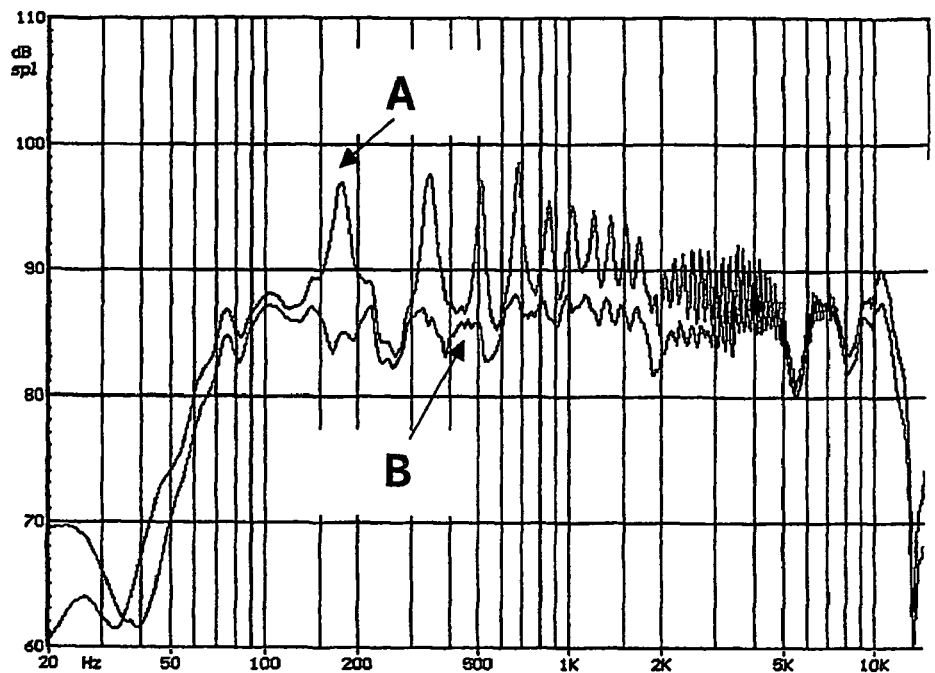
FIG. 3 shows the range of frequencies measured using the laboratory design depicted in FIG. 2.

FIG. 1*a*) schematically shows the interior of a motor vehicle with two individual seats, driver and front passenger seats, and a bench seat in the back. Within such a typical vehicle interior, the dissemination of the from a loudspeaker signal radiated in the center above the bench seat's back rest has been measured. FIG. 1*b*) shows the power drop in the loudspeaker signal as a function of distance. In this context, curve 11 shows the power drop in the direction 10 of the driver and of the front passenger seat and curve 13 shows the power drop in the direction 12 of the passengers on the back seat at an angle of 45° from the loudspeaker. It can clearly be seen that the sound power drops by 6 dB whenever the distance is doubled. This applies to the unweighted level and to the A weighting (the A weighting takes into account the subjective hearing sensitivity in a coarse approximation). The 6 dB value is the correct value if we are in the direct sound field of the sources. This condition is met approximately in the vehicle up to the measured distance of 80 cm. An ideal diffuse sound field (e.g. as a result of a very large number of reflections) would have no location dependency. Since we achieve this 6 dB value in the vehicle, it makes sense to place the sound source directly by the user, that is to say on his headrest, so that the other occupants can now overhear only a little sound as a result of greater distances. By way of example, the user is at a distance of 5 cm from the sound source whereas the next other listener is at a distance of 40 cm. This means that the sound power is 18 dB lower for the other listener. A fundamental aspect of the invention is that the reduction in overhearing as a result of the distance dependency is obtained in the direct, near sound field.

FIG. 2 shows the laboratory design for an arrangement comprising a pressure chamber loudspeaker and a thin-walled plastic tube connected thereto. The plastic tube 20 has an internal diameter of 15 mm and is 1 meter long. The loudspeaker 21 used in the laboratory system is a test loudspeaker from the company B&K. In this context, the pressure chamber loudspeaker comprises a loudspeaker chassis in a small pressure-tight housing. The air volume on the front 22 of the loudspeaker's diaphragm up to the tube attachment is very small. At a distance of approximately 10 cm perpendicularly in front of the tube opening, a test microphone 23 has been placed. This arrangement was set up to form measurements in an acoustically damped room.

FIG. 3 shows two frequency response measurements which have been performed using the laboratory design depicted in FIG. 2.

In this context, curve A represents the measurement curve produced from operating the design without covering the sound line. Curve A shows significant resonances at 170, 340, 510, 680, . . . Hz. The resonances are obtained at the frequencies at which the wavelength is twice the tube length (and integer fractions thereof).

Curve B describes the frequency response of the design when the sound line is terminated, in line with the invention, with a 35 rayl felt metal 24. In this context, it becomes clear that the resonances are reduced by approximately 10 dB and hence an approximately straight (linear) frequency response is produced.

Figure 4:
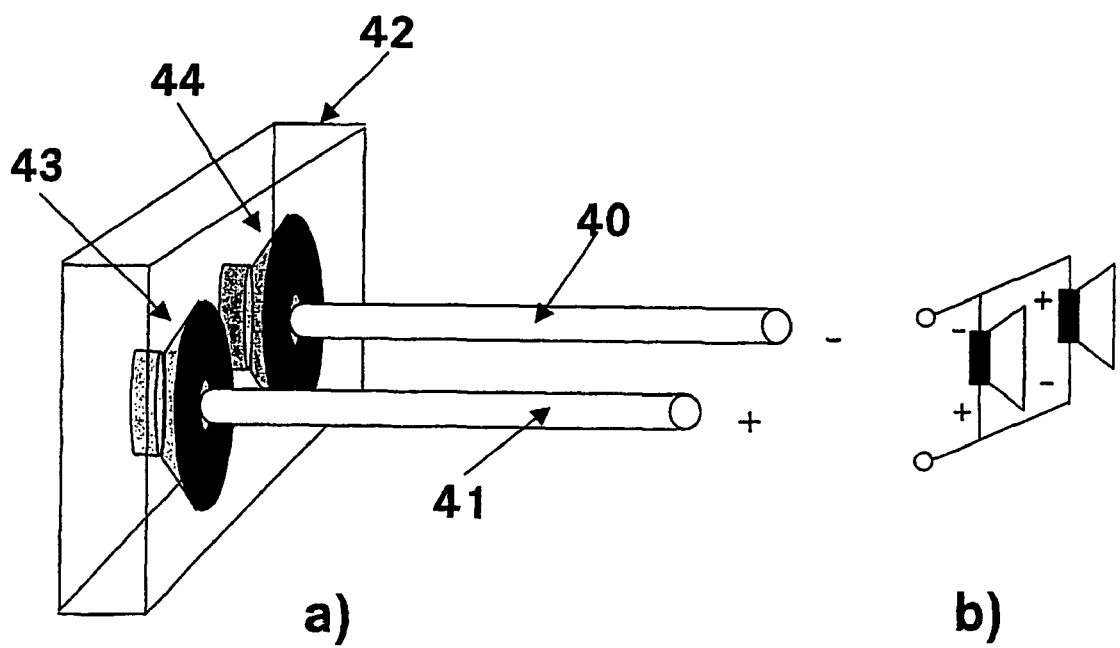
FIG. 4 shows an example of a sound transducer in the form of an isobaric push/pull system.

The discussion below demonstrates how an acoustically managed loudspeaker system is used to produce directivity. In this case, FIG. 4*a*) schematically shows a sound transducer comprising two tubes 40 and 41, a housing 42 and two identical loudspeaker chassis 43 and 44. The installation of the two chassis 43 and 44 in the housing 42 corresponds to an isobaric push/pull system. The push/pull function is achieved by virtue of the two chassis being connected in electrical antiphase, so that the diaphragm movements are contrary. The air volume between the front of the diaphragm and the tube attachment is very small. There is virtually always the same constant pressure in the cabinet and a swinging antiphase pressure in the tubes. This arrangement produces a dipole loudspeaker in practice, with two antiphase punctiform sound sources representing the openings of the two tubes. FIG. 4*b*) shows the equivalent electrical circuit diagram describing the actuation of the two loudspeaker chassis 43 and 44. To avoid resonance effects as a result of the tubes, the tube ends can again be terminated with an acoustic material having a value of approximately 40 rayl.

Figure 5:
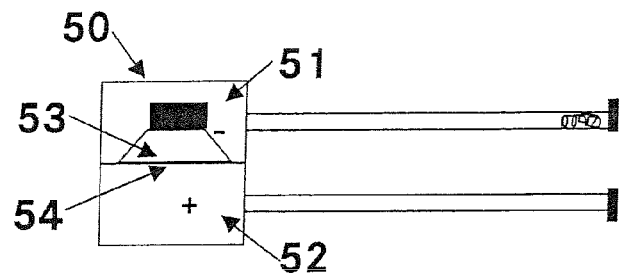
FIG. 5 outlines an alternative design for an isobaric push/pull system.

FIG. 5 outlines an alternative design for an isobaric push/pull system which has the advantage that it utilizes the dipole characteristic of an individual loudspeaker chassis 50. In this context, the loudspeaker housing is divided into two chambers 51 and 52, which are respectively associated with the front 53 of the diaphragm and with the back 54 of the diaphragm. This always results in an antiphase pressure in the two chambers, which is distinguished by "+" and "−". In comparison with the isobaric push/pull system from FIG. 4, the design is simpler in this context and only a single loudspeaker chassis is required. In this case, it may be more difficult to set the same acoustic conditions at the tube ends, however, since the loudspeaker chassis itself is asymmetric and hence acoustically different conditions may sometimes be present at the start of the tube.

Figure 6:
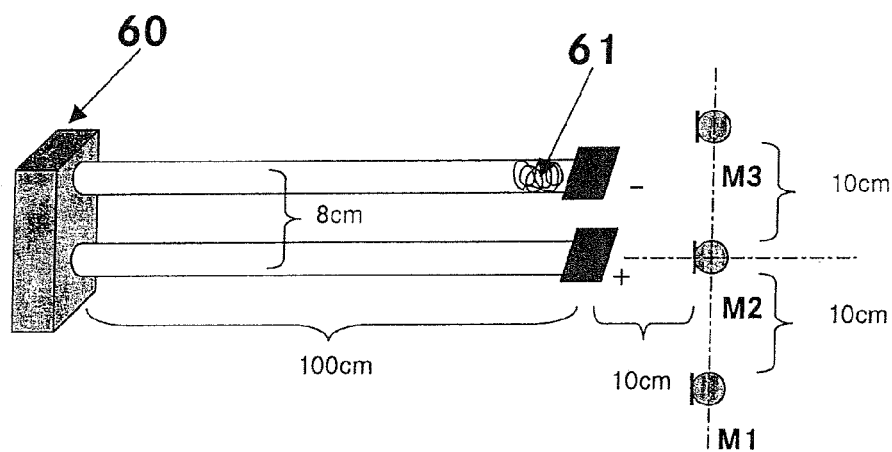
FIG. 6 shows a laboratory design for ascertaining the directivity of an acoustic apparatus whose sound transducer operates on the basis of a push/pull system.

FIG. 6 schematically shows the laboratory design for gauging an isobaric push/pull system 60 with acoustic termination of the tube ends. One of the tubes additionally contains damping material 61 at the end in order to reduce the sound emerging from this tube over a wide bandwidth. In the present example, the emergence of sound has been reduced by approximately 3 dB over a wide bandwidth by fibrous damping material. Three test microphones M1, M2 and M3 are in position for the purpose of measuring the directivity of the arrangement. The symbol "+" is intended to denote the useful sound source, and "−" denotes the antiphase compensating sound source. The loudspeaker chassis used in this case are simple systems which are used for inexpensive products, such as television sets. The housing has not been acoustically optimized. This system can be used to show wideband directivity, for example.

Figure 7:
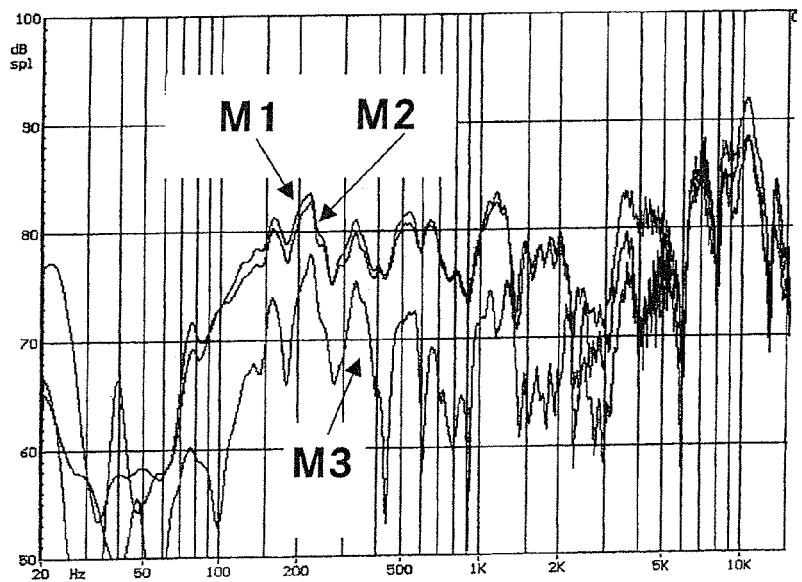
FIG. 7 shows the range of frequencies measured using the laboratory design depicted in FIG. 6.

FIG. 7 shows the frequency responses with the microphones M1, M2 and M3. An almost congruent frequency response is obtained for M1 and M2 in the range from 70 Hz to 2 kHz. The physical range around M1 and M2 is the useful range, which should contain the listener's ear. In this case, M3 is the adjoining range, which needs to receive as little sound as possible. The antiphase sound reduced by 3 dB results in partial cancellation in this case, which means that 10 dB less sound is available over a wide bandwidth. The adjoining range, which is intended to receive the acoustic signal as little as possible, has been set by selecting the 3 dB damping with a damping material 61 in the above example. If the adjoining range needs to be at a greater distance from the useful range, this can be set by two measures. The physical distance between the tube openings (8 cm in the example above) is increased or the 3 dB damping value is reduced, for example to between 1 and 2 dB. The test results shown in FIG. 7 are naturally merely examples, and it goes without saying that suitable acoustic optimization of the signal transmitted by the sound transducers allows the same acoustic apparatus to produce an even more uniform frequency response, and also a larger bandwidth. In the case of a tube system, besides frequency selection using an ordinary frequency selector, it is possible to influence the transmitted frequency component by means of damping materials in a tube and various tube diameters.

Setting the damping value and the distance between the tube ends allows experimental optimization for the respective instance of application. If, in a car, for example, the intention is to reduce what is overheard from the driver's headrest by the front-seat passenger, then the close range will be approximately 50 cm away from the useful range. The exact determination of the damping value and of the tube distance is also dependent on the design of the headrest. Experimental optimization is recommended in the vehicle.

Figure 8:
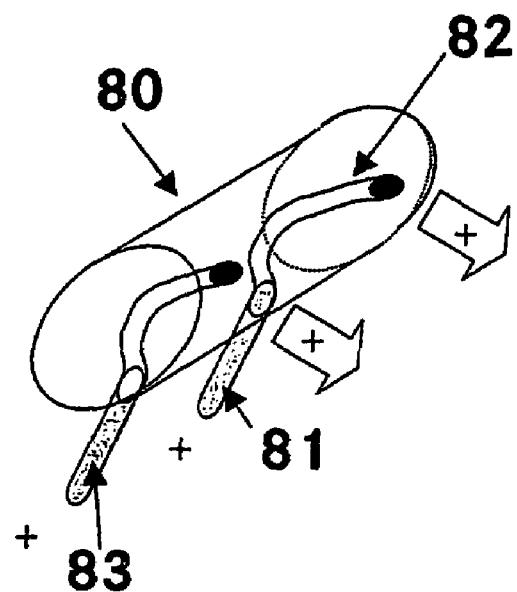
FIG. 8 shows an example of an inventive headrest with sound routing through the support rods.

FIG. 8 shows an example of an acoustic headrest 80 with sound routing. The support 81 routes the sound into the headrest. The support 81 is in the form of a tube, and from the end of the support 81 a further tube element 82 is finally routed to the opening. The openings are in direct proximity to the ears of the listener. It is particularly profitable if the second support 83 for the headrest is accordingly also in the form of a tubular sound conductor with further tube elements. Both tube systems can then receive either the same signal from a loudspeaker system or else different signals in order to produce a stereophonic effect, for example. The sound transducer used in such a system may be a pressure chamber system, for example.

Figure 9:
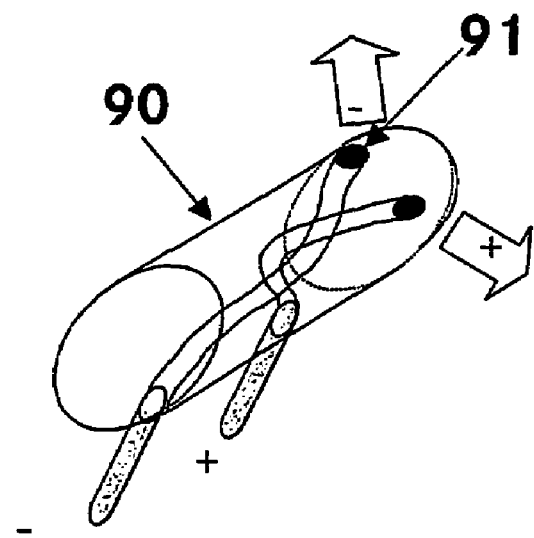
FIG. 9 shows an example of a headrest in which directivity of the radiated sound is obtained through suitable implementation of the sound routing.

FIG. 9 shows an acoustic headrest 90, with an opening 91 for the antiphase signal being provided on the back of the headrest. This figure shows only the arrangement for one side of the headrest, that is to say only for one ear. The listener's ear is intended to be reached by the sound denoted by "+". In the lateral direction or toward the back, partial compensation with the "−" sound is intended to be produced for the other listeners. It is advantageous to choose the tube lengths for the "+" and "−" sound to be the same, in order to obtain the same type of frequency responses as far as possible. The loudspeaker used in this context may advantageously be an isobaric push/pull system.

One alternative to producing directivity is to use a plurality of tubes with the same sound component and to arrange the openings of these tubes in one plane. This plane thus contains a large number of acoustic point sources to a certain extent. The sources in the plane simulate a large radiating plane. Radiating planes exhibit clear directivity if the extent of the plane reaches the order of magnitude of the acoustic wavelength. If the extent of the plane is greater than the wavelength, the delay time differences in the sources are large and hence the resultant directivity is particularly pronounced.

Figure 10:
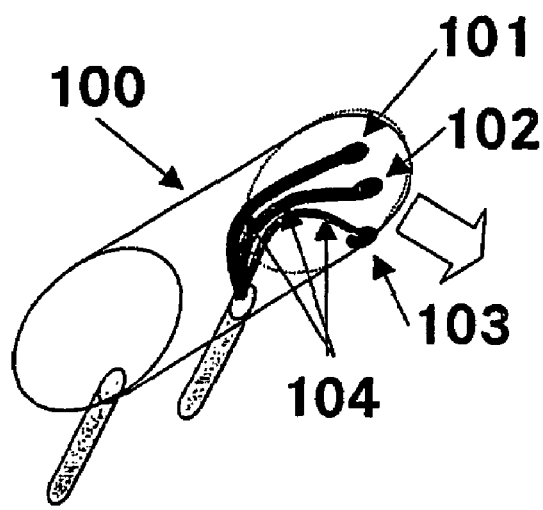
FIG. 10 shows an example of a headrest in which the sound emergence locations of the inventive apparatus are arranged to form a flat radiating element.

FIG. 10 shows a simple example of a headrest 100, with three tube ends 101, 102 and 103 contributing to the sound production and directivity. It is advantageous that the tube lines used 101, 102 and 103 are the same length in order to obtain the same acoustic properties. It is possible to use parallel-routed tube lines or a branched tube line. The three sound sources 104 are arranged above one another in the example shown in FIG. 10. The vertical arrangement of sound sources is known from auditorium sound using column loudspeakers. This achieves horizontal directivity for the arrangement and reduces the radiation of sound toward the ceiling (and toward the floor) (horizontal focusing).

If a plurality of sound sources are arranged next to one another and above one another in one plane, then not only horizontal focusing but also vertical focusing is achieved. In comparison with the known column loudspeaker, the possible arrangement of sound sources on a headrest is limited by the small surface area. By way of example, a 10 cm wavelength corresponds to a frequency of 3.4 kHz. Pronounced directivity starts when the source extends for approximately one quarter of the wavelength. A source extent of 10 cm is thus effective from wavelengths of 40 cm (and less). 40 cm correspond roughly to 1 kHz. For use in headrests with available "acoustic" planes with dimensions of 10 cm×10 cm, for example, the procedure shown with a plurality of tube openings is thus effective from approximately 1 kHz for the purposes of increased directivity. It is possible to combine directivity as a result of a plurality of in-phase tube ends and directivity with antiphase tube ends.

Figure 11:
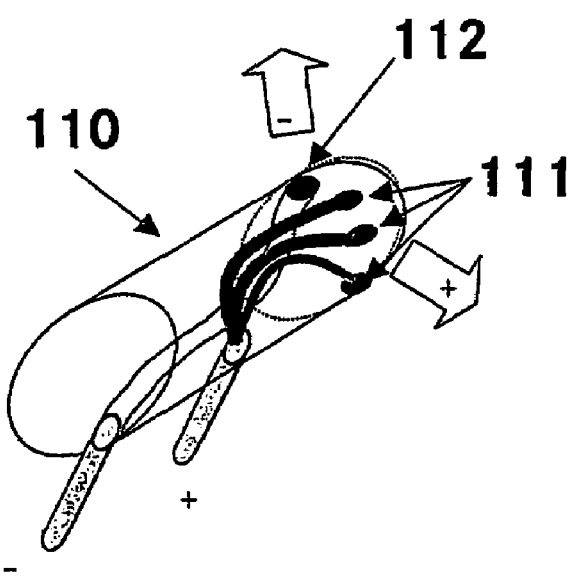
FIG. 11 shows an example of a headrest in which directivity of the emerging sound is obtained both through antiphase cancellation and through the arrangement of the sound emergence locations to form a flat panel loudspeaker.

FIG. 11 shows, by way of example, a headrest 110 which has the combination of two directional components. For midrange frequencies, e.g. from 1 kHz, the plurality of tube ends 111 on the front of the rest act as directional loudspeakers for the ear. On the back of the headrest, there is a tube end 112 with antiphase sound for canceling sound from the sides and rear. This side/rear cancellation is effective for frequencies below 1 kHz in the present case.

For high frequencies, such as those from 10 kHz, the directivity of very small ordinary piston-type loudspeakers is already very clear. At 10 kHz, the wavelength is approximately 3.4 cm. Roughly from one quarter of the diaphragm diameter, that is to say from approximately 0.8 cm, there is marked directivity. Loudspeakers with a diameter in the order of magnitude of 1 cm are thus suitable as directional loudspeakers for high frequencies.

For the acoustic headrest, there are two options for achieving directivity for high frequencies. In the case of tube diameters in the order of magnitude of 1 cm, directivity is automatically obtained for high frequencies. Alternatively, a small conventional loudspeaker may be used for high frequencies. The high frequencies are then reproduced using this small loudspeaker. Design restrictions and the risk of injury in an accident are low on account of the small loudspeaker in the order of magnitude of 1 cm diameter. The power requirement is much lower for high frequencies than for mid-range and low frequencies, which means that the small loudspeaker is also sufficient for the line requirement.

A multipath system is obtained by splitting into a tube system for mid-range and low frequencies and for a small loudspeaker for high frequencies. Multipath systems are known in loudspeaker design. They require a "frequency selector" in order to actuate the individual chassis with the signal components which are provided for them.

It goes without saying that the use of the inventive acoustic apparatus is not limited to use in a headrest but rather can be used profitably particularly where there is limited installation space for integrating acoustic sound transducers or in which it does not appear possible to integrate conventional sound transducers for safety reasons.

The invention claimed is:
1. An acoustic apparatus for producing audio signals,
   wherein the sound transducer and the at least one sound emergence location are physically separate from one another,
   in which the sound transducer is connected to the sound emergence location by means of at least one air-guiding sound conduit,
   wherein the at least one sound emergence location is provided with a means for achieving acoustic impedance matching for the air in the sound conduit and the ambient air in order to reduce resonance effects,
   wherein the means for acoustic resonance matching is made of a material which has the acoustic impedance of air, and
   wherein this material is placed in two dimensions and contiguously over the at least one sound emergence location.
2. The acoustic apparatus as claimed in claim 1, wherein the material which has the acoustic impedance of air is a fibrous and/or porous material with an acoustic impedance in the order of 41.4 rayl.
3. The acoustic apparatus as claimed in claim 1 wherein the apparatus has at least two sound conduits, where the sound emerging jointly from the sound conduit has a high sound level through superimposition in a preferred direction and has a lower sound level in an unwanted direction as a result of the design of the sound conduit and/or as a result of the manner in which the sound is supplied by the sound transducer.
4. The acoustic apparatus as claimed in claim 3, wherein the sound emergence locations of the individual sound conduit are arranged relative to one another such that a flat radiating element is produced.
5. An acoustic apparatus for producing audio signals,
   in which the sound transducer and the at least one sound emergence location are physically separate from one another,
   in which the sound transducer is connected to the sound emergence location by means of at least one air-guiding sound conduit,
   and in which the at least one sound emergence location is provided with a means for achieving acoustic impedance matching for the air in the sound conduit and the ambient air in order to reduce resonance effects,
   and the means for acoustic resonance matching is made of a material which has the acoustic impedance of air,
   wherein this material is placed in two dimensions and contiguously over the at least one sound emergence location,
   wherein the apparatus has at least two sound conduits, where the sound emerging jointly from the sound conduits has a high sound level through superimposition in a preferred direction and has a lower sound level in an unwanted direction as a result of the design of the sound conduit and/or as a result of the manner in which the sound is supplied by the sound transducer,
   wherein the sound emergence locations of the individual sound conduits are arranged relative to one another such that a flat radiating element is produced, and
   wherein the flat radiating element comprises individual conventional loudspeakers in addition to the sound emergence locations of the individual sound conduits.
6. The acoustic apparatus as claimed in claim 5, wherein the conventional loudspeakers used are small tweeters, which are suitable for radiating the high frequencies within the audible frequency range.
7. An acoustic apparatus for producing audio signals,
   in which the sound transducer and the at least one sound emergence location are physically separate from one another,
   in which the sound transducer is connected to the sound emergence location by means of at least one air-guiding sound conduit,
   and in which the at least one sound emergence location is provided with a means for achieving acoustic impedance matching for the air in the sound conduit and the ambient air in order to reduce resonance effects,
   and the means for acoustic resonance matching is made of a material which has the acoustic impedance of air,
   wherein this material is placed in two dimensions and contiguously over the at least one sound emergence location and
   wherein to produce acoustic directivity the sound emergence locations are firstly arranged like a flat panel loudspeaker, but secondly directivity is also obtained through antiphase cancellation.
8. An acoustic apparatus for producing audio signals,
   in which the sound transducer and the at least one sound emergence location are physically separate from one another,
   in which the sound transducer is connected to the sound emergence location by means of at least one air-guiding sound conduit,
   and in which the at least one sound emergence location is provided with a means for achieving acoustic impedance matching for the air in the sound conduit and the ambient air in order to reduce resonance effects,
   and the means for acoustic resonance matching is made of a material which has the acoustic impedance of air,
   wherein this material is placed in two dimensions and contiguously over the at least one sound emergence location, and
   wherein the sound transducer used is an isobaric push/pull system.
9. The acoustic apparatus as claimed in claim 1 wherein the sound emergence locations are placed in the headrests of a vehicle seat, and the sound transducers are located outside of the headrests.
10. The acoustic apparatus as claimed in claim 9, wherein the support rods of the headrests are used for acoustic sound transmission.
11. The acoustic apparatus as claimed in claim 2, wherein the material which has the acoustic impedance of air is felt, sponge material, unwoven fabric or felt metal.
12. The acoustic apparatus as claimed in claim 11, wherein the thickness of the felt metal is in the order of magnitude of 1 mm.
13. The acoustic apparatus as claimed in claim 1, wherein said at least one air-guiding sound conduit has a length of up to 1 meter.

* * * * *